United States Patent [19]
Dalbøge et al.

[11] Patent Number: 5,958,724
[45] Date of Patent: *Sep. 28, 1999

[54] PROCESS FOR PRODUCING HEME PROTEINS

[75] Inventors: Henrik Dalbøge; Ejner Bech Jensen; Karen Gjesing Welinder, all of Virum, Denmark

[73] Assignee: Novo Nordisk A/S, Bagsvaerd, Denmark

[ * ] Notice: This patent issued on a continued prosecution application filed under 37 CFR 1.53(d), and is subject to the twenty year patent term provisions of 35 U.S.C. 154(a)(2).
This patent is subject to a terminal disclaimer.

[21] Appl. No.: 08/858,933

[22] Filed: May 20, 1997

Related U.S. Application Data

[62] Division of application No. 08/315,671, Sep. 30, 1994, Pat. No. 5,744,323, which is a continuation of application No. 08/119,077, Sep. 15, 1993, abandoned.

[30] Foreign Application Priority Data

Mar. 22, 1991 [EP]  European Pat. Off. .............. 91610022

[51] Int. Cl.$^6$ .............................. C12N 15/52; C12N 9/08
[52] U.S. Cl. ...................... 435/69.1; 435/69.8; 435/69.9; 435/189; 435/192; 435/252.3; 435/254.3; 435/325; 435/320.1; 536/23.2; 536/23.74
[58] Field of Search .................................. 435/69.1, 69.8, 435/69.9, 185, 192, 252.3, 254.3, 320.1, 325; 536/23.2, 23.74

[56] References Cited

FOREIGN PATENT DOCUMENTS 0 215 594  3/1987  European Pat. Off. .
0 238 023  9/1987  European Pat. Off. .

OTHER PUBLICATIONS

Saunders et al., Tibtech, vol. 7, pp. 283–287 (1989).
Van Brunt, Bio/Technology, vol. 4, No. 12, pp. 1057–1062 (1986).
Yasumori et al., Molecular Pharmacology, vol. 35, No. 4, pp. 443–449 (1989).
Smith et al., J. Biological Chem., vol. 265, No. 22, pp. 13335–133343 (1990).
Wang et al., J. of Biotechnology, vol. 13, pp. 131–144 (1990).
Ortlepp et al., J. Biotechnology, vol. 11, pp. 353–364 (1989).
Loprasert et al., J. Bacteriology, vol. 171, No. 9, pp. 4871–4875 (1989).
Hoffman et al., Proc. Natl. Acad. Sci. USA, vol. 87, pp. 8521–8525 (1990).

*Primary Examiner*—Karen Cochrane Carlson
*Attorney, Agent, or Firm*—Steve T. Zelson, Esq.; Reza Green, Esq.

[57] ABSTRACT

The present invention relates to methods for producing heterologous heme proteins extracellularly comprising transforming a filamentous fungus with a vector comprising a DNA sequence encoding the heterologous heme protein and a DNA sequence encoding a preregion permitting secretion of the expressed heme protein, and culturing the transformed filamentous fungus in a suitable culture medium to produce the heme protein.

11 Claims, 3 Drawing Sheets

```
        10         20         30         40         50         60
         |          |          |          |          |          |
TACTATGAAGCTCTCGCTTTTGTCCACCTTCGCTGCTGTCATCATCGGTGCCCTCGCTCT 70         80         90        100        110        120
         |          |          |          |          |          |
ACCCCAGGGTCCTGGAGGAGGCGGGTCAGTCACTTGCCCCGGTGGACAGTCCACTTCGAA 130        140        150        160        170        180
         |          |          |          |          |          |
CAGCCAGTGCTGCGTCTGGTTCGACGTTCTAGACGATCTTCAGACCAACTTCTACCAAGG 190        200        210        220        230        240
         |          |          |          |          |          |
GTCCAAGTGTGAGAGCCCTGTTCGCAAGATTCTTAGAATTGTTTTCCATGACGCGATCGG 250        260        270        280        290        300
         |          |          |          |          |          |
ATTTTCGCCGGCGTTGACTGCTGCTGGTCAATTCGGTGGTGGAGGAGCTGATGGCTCCAT 310        320        330        340        350        360
         |          |          |          |          |          |
CATTGCGCATTCGAACATCGAATTGGCCTTCCCGGCTAATGGCGGCCTCACCGACACCGT 370        380        390        400        410        420
         |          |          |          |          |          |
CGAAGCCCTCCGCGCGGTCGGTATCAACCACGGTGTCTCTTTCGGCGATCTCATCCAATT 430        440        450        460        470        480
         |          |          |          |          |          |
CGCCACTGCCGTCGGCATGTCCAACTGCCCTGGCTCTCCCCGACTTGAGTTCTTGACGGG 490        500        510        520        530        540
         |          |          |          |          |          |
CAGGAGCAACAGTTCCCAACCCTCCCCTCCTTCGTTGATCCCCGGTCCCGGAAACACTGT 550        560        570        580        590        600
         |          |          |          |          |          |
CACTGCTATCTTGGATCGTATGGGCGATGCAGGCTTCAGCCCTGATGAAGTAGTTGACTT
```

Fig. 1a

```
          610       620       630       640       650       660
           |         |         |         |         |         |
GCTTGCTGCGCATAGTTTGGCTTCTCAGGAGGGTTTGAACTCGGCCATCTTCAGGTCTCC 670       680       690       700       710       720
           |         |         |         |         |         |
TTTGGACTCGACCCCTCAAGTTTTCGATACCCAGTTCTACATTGAGACCTTGCTCAAGGG 730       740       750       760       770       780
           |         |         |         |         |         |
TACCACTCAGCCTGGCCCTTCTCTCGGCTTTGCAGAGGAGCTCTCCCCCTTCCCTGGCGA 790       800       810       820       830       840
           |         |         |         |         |         |
ATTCCGCATGAGGTCCGATGCTCTCTTGGCTCGCGACTCCCGAACCGCCTGCCGATGGCA 850       860       870       880       890       900
           |         |         |         |         |         |
ATCCATGACCAGCAGCAATGAAGTTATGGGCCAGCGATACNNNNNNNNNCATGGCCAAGAT 910       920       930       940       950       960
           |         |         |         |         |         |
GTCTGTTCTCGGCTTCGACAGGAACGCCCTCACCGATTGCTCTGACGTTATTCCTTCTGC 970       980       990      1000      1010      1020
           |         |         |         |         |         |
TGTGTCCAACAACGCTGCTCCTGTTATCCCTGGTGGCCTTACTGTCGATGATATCGAGGT 1030      1040      1050      1060      1070      1080
           |         |         |         |         |         |
TTCGTGCCCGAGCGAGCCTTTCCCTGAAATTGCTACCGCCTCAGGCCCTCTCCCCTCCCT 1090      1100      1110      1120      1130      1140
           |         |         |         |         |         |
CGCTCCTGCTCCTTGATCTCCTCAAGATGGTACATCCTGCTCTCTCATCATCCCTCTTAG 1150      1160      1170      1180      1190      1200
           |         |         |         |         |         |
CTATTTATCCAATCTATCTACCTATCTATGCAGTTTCTGTTCTATCACCACAGGAAGCAA 1210      1220      1230      1240      1250      1260
           |         |         |         |         |         |
GAAAGAAAAACAACAATGCAACGTGAGCAGAAATCAGCAAAAAAATAAATCAGTATACTA 1270      1280      1290      1300      1307
           |         |         |         |         |
CAGTAATGAGGCCAGTTTGCGTGGTGTCAGAAGTAAGTACGACTCGG
```

PROCESS FOR PRODUCING HEME PROTEINS

This application is a divisonal application of application Ser. No. 08/315,671 filed Sep. 30, 1994, now U.S. Pat. No. 5,744,323, which is a continuation of U.S. Ser. No. 08/119,077 filed Sep. 15, 1993 now abandoned, and claims priority of EP application Serial No. 91610022.5 filed Mar. 22, 1991, the contents of which are fully incorporated herein by reference in their entirety.

FIELD OF INVENTION

The present invention relates to a process for producing heterologous heme proteins in filamentous fungi.

BACKGROUND OF THE INVENTION

The cloning and expression of varius heme proteins in bacteria has previously been described. Thus, S. A. Ortlepp et al., *J. Biotechn.* 11, 1989, pp. 353–364, describe the expression and characterisation of horseradish peroxidase C in *E. coli*. The enzyme is expressed intracellularly as an insoluble aggregate so that it has to be purified from lysed cells. Furthermore, the enzyme is not expressed in active form and must be folded separately in the presence of heme and $Ca^{2+}$ to become functional. Similarly, A. T. Smith et al., *J. Biol. Chem.* 265(22), 1990, pp. 13335–13343, describe the expression of horseradish peroxidase C in *E. coli*. The recombinant enzyme has less activity than native horseradish peroxidase C and is produced in a yield of 2–3% (of the purified, active enzyme). S. Loprasert et al., *J. Bact.* 171(9), 1989, pp. 4871–4875, report the cloning and expression in *E. coli* of peroxidase A from *Bacillus stearothermophilus*. S. J. Hoffman et al., *Proc. Natl. Acad. Sci. USA* 87, pp. 8521–8525, describe the expression of functional human hemoglobin in *E. coli*. Z. Wang et al., *J. Biotechn.* 13, 1990, pp. 131–144, describe the cloning and expression of lignin peroxidase from *Streptomyces viridosporus* in *Streptomyces lividans*.

Expression of human hemoglobins in yeast (*Saccharomvces cerevisiae*) has been described by M. Wagenbach et al, *Bio/Technology* 9, 1991, pp. 57–61. In yeast, hemoglobin is expressed as a fully assembled, heme-containing tetramer. However, the protein is not secreted from the yeast cells, but remains in the cytoplasmic space and must be purified therefrom.

It would therefore be advantageous to select a host organism, such as a filamentous fungus, which is capable not only of producing heme proteins but also of exporting them through the cell membrane in active form, thereby simplifying purification procedures.

In recent years, procedures have been developed for the transformation of filamentous fungi, including *Aspergillus niger* and *Aspergillus nidulans*. U.S. Pat. No. 4,885,249 (Allelix) describes a general process for the transformation of *A. niger*, exemplified by the introduction of plasmids carrying genes encoding selectable markers. EP 215 594 (Genencor) describes the expression and secretion of various proteins in *A. nidulans*, using the signal sequences of different Aspergillus proteins to provide secretion.

Neither of these references indicates the possibility of producing heme proteins in filamentous fungi. On the contrary, M. Saloheimo et al., *Gene* 85, 1989, pp. 343–351, describe the cloning and expression of a lignin peroxidase from *Phlebia radiata* in *Trichoderma reesei*. The authors report that although lignin peroxidase mRNA is expressed in *T. reesei*, no protein product could be detected. They speculate that this might be ascribable to intracellular degradation by proteases due to incorrect folding of the protein in the absence of heme or to a different structure of the RNA interfering with its translation.

SUMMARY OF THE INVENTION

It has surprisingly been found that heme proteins may be produced in filamentous fungi in yields which far exceed those obtainable for the same protein in yeast.

Accordingly, the present invention relates to a process for the extracellular production of a heterologous heme protein in a filamentous fungus, the process comprising (a) transforming a suitable filamentous fungus with a recombinant DNA vector which comprises a DNA sequence encoding a heterologous heme protein, and a DNA sequence encoding a preregion permitting secretion of the expressed heme protein, and (b) culturing the transformed filamentous fungus in a suitable culture medium under conditions conducive to the production of the heme protein.

In the present context, the term "extracellular production" is understood to indicate that, contrary to the known methods of producing heme proteins in bacteria or yeast, the heme protein is secreted from the host cell into the culture medium and may readily be recovered therefrom. Apparently, the recombinant protein is able to incorporate heme produced by the heme synthetic pathway of the fungal host and may therefore be secreted by the host cell as a fully assembled, heme-containing protein. The term "heterologous" is meant to indicate proteins which are not, in nature, produced by the host organism in question. The term "heme protein" is intended to include any member of a group of proteins containing heme (e.g. protoporphyrin IX) as a prosthetic group. The term "filamentous fungus" is intended to include fungi belonging to the groups Phycomycetes, Zygomycetes, Ascomycetes, Basidiomycetes or fungi imperfecti, icluding Hyphomycetes such as the genera Aspergillus, Trichoderma, Penicillium, Fusarium or Humicola.

DETAILED DESCRIPTION OF THE INVENTION

The vector conveniently comprises DNA sequences encoding functions facilitating gene expression, typically a promoter, transcription initiation sites, and transcription termination and polyadenylation functions.

The promoter which may be preceded by upstream activating sequences and enhancer sequences as known in the art may be any DNA sequence exhibiting a strong transcriptional activity in filamentous fungi and may be derived from a gene encoding an extracellular or intracellular protein such as an amylase, a glucoamylase, a protease, a lipase, a cellulase or a glycolytic enzyme.

Examples of suitable promoters are those derived from the gene encoding *A. oryzae* TAKA amylase, *Rhizomucor miehei* aspartic proteinase, *A. niger* neutral α-amylase, *A. niger* acid stable α-amylase, *A. niger* glucoamylase, *Rhizomucor miehei* lipase, *A. oryzae* alkaline protease or *A. oryzae* triose phosphate isomerase.

The filamentous fungus host organism may conveniently be one which has previously been used as a host for producing recombinant proteins, e.g. a strain of Aspergillus sp., such as *A. niger, A. nidulans* or *A. oryzae*. The use of *A. oryzae* in the production of recombinant proteins is extensively described in, e.g. EP 238 023.

In particular when the host organism is *A. oryzae*, a preferred promoter for use in the process of the present invention is the *A. oryzae* TAKA amylase promoter as it exhibits a strong transcriptional activity in *A. oryzae*. The sequence of the TAKA amylase promoter appears from EP 238 023.

Termination and polyadenylation sequences may suitably be derived from the same sources as the promoter.

The techniques used to transform a fungal host cell may suitably be adapted from the methods of transforming *A. nidulans* described in, for instance, Yelton et al., *Proc. Natl. Acad. Sci. USA* 81, 1984, pp. 1470–1474, or EP 215 594, or from the methods of transforming *A. niger* described in, for instance Buxton et al., *Gene* 37, 1985, pp. 207–215 or U.S. Pat. No. 4,885,249, or from the method of transforming *A. oryzae* described in EP 238 023. In the process of the present invention, the host cell may be transformed with a vector system comprising a DNA sequence coding for a selection marker which is capable of being incorporated in the genome of the host organism on transformation, but which is either not expressed by the host before transformation or expressed in amounts which are not sufficient to permit growth under selective conditions. Transformants can then be selected and isolated from nontransformants on the basis of the incorporated selection marker.

Suitable selection markers may be derived from the *A. nidulans* or *A. niger* argB gene, the *A. nidulans* trpC gene, the *A. nidulans* amdS gene, the *Neurospora crassa* pyr4 or DHFR genes, or the *A. niger* or *A. oryzae* niaD gene.

Preferred selection markers for use in the present invention are derived from the *A. nidulans* or *A. niger* amdS or argB genes. Wild-type *A. oryzae* strains are usually ArgB+ (which means that the arqB gene is expressed in *A. oryzae*). Thus, if argB is chosen as the selection marker, an ArgB− mutant strain of *A. oryzae* (which does not express the ArqB gene) must be used as the host organism. On the other hand, the amdS gene may be used as the selection marker in wild-type *A. oryzae* strains which do not express this gene in sufficient amounts to permit growth under selective conditions.

The preregion provided on the vector to ensure efficient direction of the expressed product into the secretory pathway of the host cell may be a naturally occurring signal or leader peptide or a functional part thereof or a synthetic sequence providing secretion of the protein from the cell. Thus, the preregion may be derived from a gene coding for a secreted protein derived from any source.

In particular, the preregion may be derived from a gene encoding an Aspergillus sp. amylase or glucoamylase, a gene encoding a *Rhizomucor miehei* lipase or protease, or a gene encoding a Coprinus sp. peroxidase.

The preregion is preferably derived from the gene encoding *A. oryzae* TAKA amylase, *A. niger* neutral α-amylase, *A. niger* acidstable α-amylase, *A. niger* glucoamylase, or a *Coprinus macrorhizus* or *cinereus* peroxidase.

The DNA sequences coding for the heme protein, preregion, promoter and terminator may be inserted in a vector containing a selection marker, or it may be inserted in a separate vector for introduction into the host cell. The vector or vectors may be linear or closed circular molecules. In one embodiment of the process of the invention, two vectors, one carrying the DNA sequence coding for the selection marker, and the other carrying the DNA sequences encoding the heme protein, the preregion and the functions facilitating gene expression, may be introduced into the host cell.

The heme protein produced by the process of the present invention is preferably an oxidoreductase, in particular a peroxidase, including a lignin peroxidase or Mn-peroxidase, or haloperoxidase. In a currently preferred embodiment, the DNA sequence encoding the peroxidase is derived from a Coprinus sp., in particular *Coprinus macrorhizus* or *cinereus*.

In another aspect, the present invention relates to a DNA construct comprising the DNA sequence shown in FIG. 1A–1B encoding a Coprinus sp. peroxidase, or a suitable modification thereof.

Examples of suitable modifications of the DNA sequence are nucleotide substitutions which do not give rise to another amino acid sequence of the peroxidase, but which correspond to the codon usage of the host organism into which the DNA construct is introduced or nucleotide substitutions which do give rise to a different amino acid sequence and therefore, possibly, a different protein structure which might give rise to a peroxidase mutant with different properties than the native enzyme. Other examples of possible modifications are insertion of one or more nucleotides into the sequence, addition of one or more nucleotides at either end of the sequence, or deletion of one or more nucleotides at either end or within the sequence.

The DNA construct of the invention encoding the peroxidase may be prepared synthetically by established standard methods, e.g. the phosphoamidite method described by S. L. Beaucage and M. H. Caruthers, *Tetrahedron Letters* 22, 1981, pp. 1859–1869, or the method described by Matthes et al., *EMBO Journal* 3, 1984, pp. 801–805. According to the phosphoamidite method, oligonucleotides are synthesized, e.g. in an automatic DNA synthesizer, purified, annealed, ligated and cloned in suitable vectors.

The DNA construct of the invention may also be of genomic or cDNA origin, for instance obtained by preparing a genomic or cDNA library and screening for DNA sequences coding for all or part of the peroxidase by hybridization using synthetic oligonucleotide probes in accordance with standard techniques (cf. Sambrook et al., *Molecular Cloning: A Laboratory Manual*, 2nd Ed., Cold Spring Harbor, 1989) In this case, a genomic or cDNA sequence encoding the peroxidase may be modified at a site corresponding to the site(s) at which it is desired to introduce amino acid substitutions, e.g. by site-directed mutagenesis using synthetic oligonucleotides encoding the desired amino acid sequence for homologous recombination in accordance with well-known procedures.

Finally, the DNA construct may be of mixed synthetic and genomic, mixed synthetic and CDNA or mixed genomic and CDNA origin prepared by ligating fragments of synthetic, genomic or CDNA origin (as appropriate), the fragments corresponding to various parts of the entire DNA construct, in accordance with standard techniques. The DNA construct may also be prepared by polymerase chain reaction using specific primers, for instance as described in U.S. Pat. No. 4,683,202 or R. K. Saiki et al., *Science* 239, 1988, pp. 487–491.

The invention further relates to a recombinant expression vector into which the DNA construct of the invention is inserted. This may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

In the vector, the DNA sequence encoding the peroxidase should be operably connected to a suitable promoter and terminator sequence. The promoter may be any DNA sequence which shows transcriptional activity in the host cell of choice and may be derived from genes encoding proteins either homologous or heterologous to the host cell. Examples of suitable promoters are those indicated above. The procedures used to ligate the DNA sequences coding for the peroxidase, the promoter and the terminator, respectively, and to insert them into suitable vectors are well known to persons skilled in the art (cf., for instance, Sambrook et al., op.cit.).

The invention also relates to a host cell which is transformed with the the expression vector of the invention. The host cell is a cell of a filamentous fungus, and is preferably a cell of an Aspergillus sp. as indicated above.

The medium used to culture the transformed host cells may be any conventional medium suitable for growing filamentous fungi. The transformants are usually stable and may be cultured in the absence of selection pressure. However, if the transformants are found to be unstable, a selection marker introduced into the cells may be used for selection. It has surprisingly been found that if hemin or a heme-containing material (e.g. hemoglobin or red blood cells) is added to the medium, the yield of heme protein may be significantly increased (cf. Examples 3–6 below).

The mature heme protein secreted from the host cells may conveniently be recovered from the culture medium by well-known procedures including separating the cells from the medium by centrifugation or filtration, and precipitating proteinaceous components of the medium by means of a salt such as ammonium sulphate, followed by chromatographic procedures such as ion exchange chromatography, affinity chromatography, or the like.

BRIEF DESCRIPTION OF THE DRAWINGS

The invention is described in the following examples with reference to the appended drawings, wherein FIG. 1A–1B shows the cDNA sequence encoding a *Coprinus cinereus* peroxidase.

Figure 2:
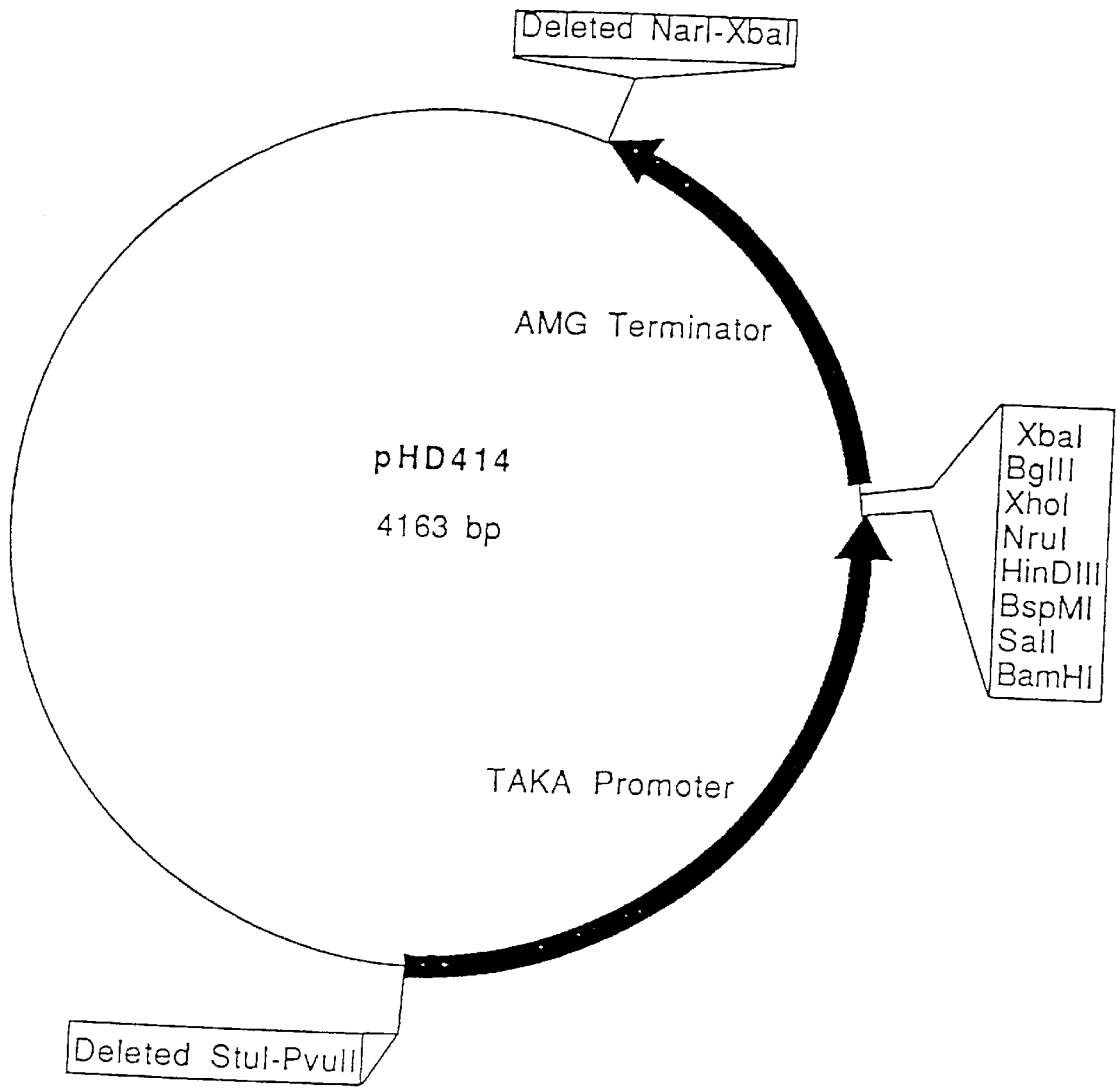
FIG. 2 is a map of the vector pHD414.

The invention is further illustrated in the following examples which are not in any way to be construed as limiting to the scope of the invention as claimed.

EXAMPLE 1

Cloning of cDNA encoding a *Coprinus cinereus* peroxidase

Construction of a probe by PCR

Peroxidase CDNA fragments were prepared by polymerase chain reaction (PCR) using specific oligonucleotide primers (R. K. Saiki et al. *Science* 239, 1988, pp. 487–491) constructed on the basis of the amino acid sequence of the *Coprinus macrorhizus* peroxidase. PCR was carried out using the Gene Amp kit and apparatus (available from Perkin Elmer Cetus, Norwalk, Conn., USA) in accordance with the manufacturer's instructions, with the exception that the reaction was conducted at 28° C. for the first three cycles in order to obtain better hybridisation to the first strand CDNA (prepared from mRNA obtained from *Coprinus cenereus*, IFO 8371) and subsequently at 65° C. for 30 cycles of PCR.

The following specific primers were used for PCR:

```
                   T   T
1. 5'-GCGCGAATTCGTNGGNATNAACCACGG-3'

A  A
2. 3'-TACAGNTTGACGGGNGGCCTAGGCG-5'

A      T T
3. 5'-GCGAATTCACNCCNCAGGTNTTCGACAC-3'

A       T  A
4. 3'-GGNAAGGGNCCNCTCAAGCCTAGGCG-5'

A
5. 5'-GCGCGAATTCTGGCAGTCNAC-3'

A
6. 5'-GCGCGAATTCTGGCAGAGNATG-3'

T
7. 3'-CGNTACCGNTTCTACAGCCTAGG-5'
```

"N" denoting a mixture of all four nucleotides.

The primers were combined as follows: 1 with 2, 3 with 4, 5 with 7, 6 with 7, 1 with 4, 1 with 7 and 3 with 7. The PCR fragments were thus extended with an EcoRI site at the 5'-end and a BamHI site at the 3'-end. The PCR reactions were analysed on a 1% agarose gel. Bands of the expected size were found in all reactions. To verify that the bands corresponded to peroxidase-specific sequences, the gel was subjected to Southern blotting and hybridised to an oligonucleotide probe with the following sequence

```
         T  A  A  A  T
5'-GTCTCGATGTAGAACTG-3'
         T
``` which is positioned between PCR primers 3 and 4. The probe was found to hybridise to bands of approximately 130 bp, 420 bp, 540 bp and 240 bp, thus confimrming that the DNA bands observed correspond to peroxidase sequences.

DNA from the various PCR reactions was digested with EcoRI and BamHI and cloned into the plasmid pUC19 (C. Yanisch-Perron et al., *Gene* 33, 1985, pp. 103–119). Colonies containing the correct PCR fragments were identified by hybridisation using the oligonucleotide probe specified above. DNA from positive colonies was analysed by restriction enzyme mapping and partial DNA sequence analysis as described by Sanger et al. *Proc. Natl. Acad. Sci. USA* 74, 1977, pp. 5463–5467. A 430 bp fragment from one of the clones, obtained by using primer 1 and 4, was used to screen a Coprinus cinereus cDNA library as described below.

Construction of a *Coprinus cinereus* CDNA library in *E. coli*

Total RNA was extracted from homogenized *Coprinus cinereus* (IFO 8371) mycelium, collected at the time for maximum activity of the peroxidase by methods as described by Boel et al. (EMBO J., 3: 1097–1102, 1984) and Chirgwin et al. (Biochemistry (Wash), 18: 5294–5299, 1979). Poly(A)-containing RNA is obtained by two cycles of affinity chromatography on oligo(dT)-cellulose as described by Aviv and Leder (PNAS, USA 69:1408–1412, 1972). CDNA is synthesized by means of a cDNA synthesis kit from Invitrogen according to the manufacturer's instructions. About 50.000 *E. coli* recombinants from the *Coprinus cinereus* cDNA library were transferred to Whatman 540 paper. filters. The colonies were lysed and immobilized as described by Gergen et al. (Nucleic Acids Res. 7, 2115–2135, 1979). The filters were hybridized with the $^{32}$P-labelled 430 bp peroxidase-specific probe in 0.2×SSC, 0.1% SDS. Hybridization and washing of the filters was conducted at 65° C. followed by autoradiography for 24 hours with an intensifier screen. After autoradiography, the filters were washed at increasing temperatures followed by autoradiography for 24 hours with an intensifier screen. In this way, more than 50 positive clones were identified. Miniprep plasmid DNA was isolated from hybridizing colonies by standard procedures (Birnboim and Doly Nucleic Acids Res. 7, 1513–1523, 1979), and the DNA sequence of the cDNA insert was determined by the Sanger dideoxy procedure (Sanger et al., Proc. Natl. Acad. Sci. USA 74, 1977, pp. 5463–5467). The peroxidase cDNA fragment was exised from the vector by cleavage with HindIII/XhoI and was purified by agarose gel electrophoresis, electroeluted and made ready for ligation reactions. The cDNA fragment was ligated to HindIII/XhoI digested pHD414 to generate pcip in which the cDNA is under transcriptional control of the TAKA promotor from *Aspergillus oryzae* and the AMG terminator from *Aspergillus niger*.

Construction of the Aspergillus expression vector pHD414

The vector pHD414 is a derivative of the plasmid p775 (described in EP 238 023). In contrast to p775, pHD414 has a string of unique restriction sites between the promotor and the terminator.

The plasmid was constructed by removal of an approximately 200 bp long fragment (containing undesirable restriction sites) at the 3' end of the terminator, and subsequent removal of an approximately 250 bp long fragment at the 5' end of the promotor, also containing undesirable restriction sites. The 200 bp region was removed from p775 by cleavage with NarI (positioned in the pUC vector) and XbaI (positioned just 3' to the terminator), subsequent filling in the generated ends with Klenow DNA polymerase+dNTP, purification of the vector fragment on gel and religation of the vector fragment. The DNA was transformed into *E. coli* MC1061 as described above. 10 colonies (pHD413-1 to -10) were selected and analyzed by restriction enzyme analysis. One of the clones exhibiting the expected band pattern in the restriction enzyme analysis was used in the construction of pHD414.

pHD413 was cut with StuI (positioned in the 5' end of the promoter) and PvuII (positioned in the pUC vector) and fractionated on a gel. The vector fragment was purified, religated and transformed into *E. coli* MC1061. 12 colonies were selected and analyzed by restriction enzyme analysis. All 12 clones exhibited the expected band pattern. The plasmid pHD414 is shown in FIG. 2.

Transformation of *Aspergillus oryzae* or *Aspergillus niger* (general procedure)

100 ml of YPD medium (Sherman et al., Methods in Yeast Genetics, Cold Spring Harbor Laboratory, 1981) was inoculated with spores of *A. oryzae* or *A. niger* and incubated with shaking at 37° C. for about 2 days. The mycelium was harvested by filtration through miracloth and washed with 200 ml of 0.6M $MgSO_4$. The mycelium was suspended in 15 ml of 1.2M $MgSO_4$. 10 mM $NaH_2PO_4$, pH=5.8. The suspension was cooled on ice, and 1 ml of buffer containing 120 mg of Novozym 234, batch 1687 was added. After 5 minutes 1 ml of 12 mg/ml BSA (Sigma type H25) was added, and incubation with gentle agitation was continued for 1.5–2.5 hours at 37° C. until a large number of protoplasts was visible in a sample inspected under the microscope.

The suspension was filtered through miracloth, the filtrate was transferred to a sterile tube and overlayered with 5 ml of 0.6M sorbitol, 100 mM Tris-HCl, pH=7.0. Centrifugation was performed for 15 minutes at 100 g, and protoplasts were collected from the top of the $MgSO_4$ cushion. 2 volumes of STC (1.2M sorbitol, 10 mM Tris-HCl, pH=7.5. 10 mM $CaCl_2$) were added to the protoplast suspension and the mixture was centrifuged for 5 minutes at 1000×g. The protoplast pellet. was resuspended in 3 ml of STC and repelleted. This procedure was repeated. Finally the protoplasts were resuspended in 0.2–1 ml STC.

100 μl of the protoplast suspension was mixed with 5–25 μg of the appropriate DNA in 10 μl of STC. Protoplasts from the argB strains were mixed with pSal43 DNA (an *A. nidulans* argB gene carrying plasmid) and protoplasts from the argB$^+$ strains were mixed with p3SR2 (an *A. nidulans* amdS gene carrying plasmid). The mixture was left at room temperature for 25 minutes. 0.2 ml of 60% PEG 4000 (BDH 29576), 10 mM $CaCl_2$ and 10 mM Tris-HCl, pH=7.5, were added and carefully mixed (twice) and finally 0.85 ml of the same solution was added and carefully mixed. The mixture was left at room temperature for 25 minutes, spun at 2500×g for 15 minutes and the pellet was resuspended in 2 ml of 1.2M sorbitol. After another sedimentation, the protoplasts were spread on the appropriate plates. Protoplasts from the argB strains transformed with pSal43 were spread on minimal plates (Cove Biochem.Biophys.Acta 113 (1966) 51–56) with glucose and urea as carbon and nitrogen sources, respectively, and containing 1.2M sorbitol for osmotic stabilization. Protoplasts from the argB-strains transformed with p3SR2 were spread on minimal plates (Cove Biochem-.Biophys.Acta 113 (1966) 51–56) containing 1.0M sucrose, pH=7.0, 10 mM acetamide as nitrogen source and 20 mM CsCl to inhibit background growth After incubation for 4–7 days at 37° C. spores were picked, suspended in sterile water and spread for single colonies. This procedure was repeated and spores of a single colony after the second reisolation were stored as defined transformants.

Production of recombinant *Coprinus cinereus* peroxidase in an *A. oryzae* strain pCip was transformed into *A. oryzae* A1560 (IFO 4177) by cotransformation with p3SR2 containing the amdS gene from *A. nidulans* as described above with a mixture of equal amounts of pCip and p3SR2 (approximately 5 μg of each). Transformants which are able to use acetamide as their sole nitrogen source were reisolated twice. After growth on YPD medium (Sherman et al. 1981) for three days culture supernatants were analysed by a peroxidase activity assay using ABTS (vide below). The best transformants were selected for further studies.

Production of peroxidase in *S. cerevisiae*

The peroxidase gene was isolated from pCip and introduced into the yeast expression vector pYHD5 in which the cDNA was under transcriptional control of the Gal 1–10 promoter and the α-factor terminator. A URA3 mutant yeast strain was transformed with the yeast expression plasmid by the LiAc procedure (in Yeast: A Practical Approach, I. Campbell and O. H. Duffus (eds.), IRL Press, 1988, p. 115). Transformants were selected on minimal agar plates without uracil and subsequently replica plated onto minimal agar plates without uracil, but supplemented with galactose (in order to induce the promoter) and tested for expression of peroxidase by Western blotting and by measuring the enzyme activity.

EXAMPLE 2

Comparison of the yields of *Coprinus cinereus* peroxidase from fermentation of wild-type *Coprinus cinereus* and recombinant *Coprinus cinereus* peroxidase (rCip) from fermentation of transformed *S. cerevisiae* and *A. oryzae*

Each strain used in this experiment was grown under optimised conditions and in optimised media for shake flask cultivation.

| | |
|---|---|
| *Coprinus cinereus* (IFO 8371): | Medium: 3 g/l yeast extract, 10 g/l peptone, 0.2 g/l FeSO$_4$.7H$_2$O, 1 g/l MgSO$_4$.7H$_2$O, 20 g/l glucose, pH = 7.0 Growth conditions: 30° C., 180 rpm, 7 days |
| *S. cerevisiae* (rCip): | Medium 10 g/l yeast extract, 20 g/l peptone, 10 g/l glucose, 10 g/l galactose, 0.1 g/l FeSO$_4$.7H$_2$O, pH = 5.0 Growth conditions: 30° C., 250 rpm, 4 days |
| *A. oryzae* (rCip): | Medium: 5 g/l yeast extract, 2 g/l KCl, 1 g/l NaH$_2$PO$_4$.H$_2$O, 2 g/l Na$_2$SO$_4$, 1 g/l MgCl$_2$.6H$_2$O, 2 g/l urea, 2 g/l citric acid, 0.2 g/l FeSO$_4$.7H$_2$O, 20 g/l maltose, pH = 6.0 Growth conditions: 37° C., 300 rpm, 4 days |

300 rpm, 4 days

Peroxidase activity was measured on a filtrated culture sample by a technique (described by R. E. Childs and W. G. Bardsley, *Biochem. J.* 145, 1975, pp. 93–103) involving hydrogen peroxide oxidation of ABTS (2,2'-azino-bis(3-ethylbenzthiazoline-6-sulphonic acid, supplied by Boehringer Mannheim as the diammonium salt) at pH=7.5, monitored at 418 nm. The concentration of hydrogen peroxide was 1 mM.

| Strain | Yield of extracellular peroxidase |
|---|---|
| *Coprinus cinereus* (IFO 8371) | 100% |
| rCip (*S. cerevisiae*) | 2–5% |
| rCip (*A. oryzae*) | 500% |

The advantage of using *A. oryzae* to produce *Coprinus cinereus* peroxidase is even more pronounced in fed batch fermentation where the relative yield compared to that obtained from *Coprinus cinereus* is more than 2000%.

EXAMPLE 3

Production of recombinant *Coprinus cinereus* peroxidase in an *A. oryzae* strain in a fermentation medium containing hemin pcip was transformed into *A. oryzae* A1560 (IFO 4177) by cotransformation with p3SR2 containing the amdS gene from *A. nidulans* as described above with a mixture of equal amounts of pcip and p3SR2 (approximately 5 μg of each). Transformants which are able to use acetamide as their sole nitrogen source were reisolated twice.

300 ml propylene shake flasks containing 50 ml ASP03 medium with the following composition

| | | |
|---|---|---|
| Yeast extract | 1 | g/l |
| Succinic acid | 10 | g/l |
| MgCl$_2$.6H$_2$O | 0.82 | g/l |
| KCl | 1.83 | g/l |
| NaH$_2$PO$_4$.2H$_2$O | 1.01 | g/l |
| NaSO$_4$ | 1.8 | g/l |
| Urea | 2 | g/l |
| Citric acid | 2 | g/l |
| Trace metal solution | 0.5 | ml/l |
| Pluronic | 0.1 | ml/l |
| Water up to | 1000 | ml |
| pH adjusted to 6.00 with NaOH | | | which had been autoclaved at 121° C. for 60 min. followed by addition of 20 g/l of maltodextrin and varying amounts of hemin (Sigma H-2250) dissolved in 0.01M NaOH and sterile filtered into the flasks through a 0.2 μm membrane at an alkaline pH (12), were inoculated with 1 ml of a spore suspension (approximately $10^6$ spores/ml) of *A. oryzae* transformants and incubated at 34° C. for 72 hours at 300 rpm.

The results are shown in the table below. Peroxidase activity was measured in PODU/ml. (1 PODU (peroxidase unit) is defined as the amount of enzyme that catalyses the conversion of 1 μmol H$_2$O$_2$ per minute in a system where 2,2'-azinobis[3-ethylbenzothiazoline-6-sulfonate] is oxidised in the presence of 1 mM H$_2$O$_2$, pH 7.0, at a temperature of 25° C.)

| Hemin conc. in in the medium | | Peroxidase activity after 72 hours. | |
|---|---|---|---|
| 0 | mg/l | 300 | PODU/ml |
| 1 | — | 360 | — |
| 10 | — | 680 | — |
| 100 | — | 1000 | — |
| 1000 | — | 1029 | — | appears from the table that addition of hemin to the growth medium significantly increases the peroxidase yield.

EXAMPLE 4

Production of recombinant *Coprinus cinereus* peroxidase in an *A. oryzae* strain in a fermentation medium containing hemin and a surface-active agent

*A. oryzae* transformants obtained as described above were cultured as described in Example 2 in a medium to which Glanapon DG 160 (available from Bussetti) had been added as a surface-active agent before autoclaving. The results appear from the table below.

| Heme conc. | | Glanapon conc. | | POD act. after 72 hours. | |
|---|---|---|---|---|---|
| 0 | mg/l | 0 | ml/l | 300 | PODU/ml |
| 1 | — | 0 | — | 360 | — |
| 10 | — | 0 | — | 680 | — |
| 0 | — | 5 | — | 380 | — |
| 1 | — | 5 | — | 521 | — |
| 10 | — | 5 | — | 1480 | — |

It appears from the table that the added Glanapon has an excellent synergistic effect with hemin on the peroxidase yield.

EXAMPLE 5

Production of recombinant *Coprinus cinereus* peroxidase in an *A. oryzae* strain in a fermentation medium containing hemin, hemoglobin or red blood cells

*A. oryzae* transformants obtained as described above were cultured as described in Example 2 in a medium to which hemin, hemoglobin (Merck Art 4300) or red blood cells (spray-dried mixed porcine and bovine red blood cells, food grade) has been added (before or after autoclaving). Hemoglobin and red blood cells were dissolved at pH 10.5 (NaOH) before autoclaving and sterile filtration. The results appear from the table below.

| | Peroxidase activity after 72 hours | |
|---|---|---|
| Heme source | Sterile filtered | Autoclaved 20 min. 121° C. |
| Hemin (10 mg/l) | 800 PODU/ml | 448 PODU/ml |
| Hemoglobin (1 g/l) | 1020 — | 958 — |
| Red blood cells (1 g/l) | | 903 — |

It appears from the table that heme sources, where the heme group is bound to globin results in a significant increase in the peroxidase yield. A further advantage is that they can be obtained very cheaply and that the heme group is protected against destruction during heat sterilisation.

EXAMPLE 6

Production of recombinant *Coprinus cinereus* peroxidase in an *A. oryzae* strain in a 2 liter fermentor in a fermentation medium containing hemoglobin

*A. oryzae* transformants obtained as described above were fermented in 2 liter laboratory fermentors in a fed batch process as follows:

| Tank medium: | $MgSO_4 \cdot 7H_2O$ | 2 g/l |
|---|---|---|
| | $KH_2PO_4$ | 2 g/l |
| | $K_2SO_4$ | 3 g/l |
| | Citric acid | 4 g/l |
| | Trace metals | |
| | Yeast extract | 1 g/l |
| | Pluronic | 0,2 ml/l |
| Feed medium: | Maltose | 250 g/l |
| | Yeast extract | 7 g/l |
| | $FeSO_4 \cdot 7H_2O$ | 1 g/l |
| | Urea | 20 g/l |
| | Pluronic | 2 ml/l |
| Fermentation conditions: | 2,0 l fermentors | |
| | Temp. 34° C. | |
| | pH = 7.8 | |
| | pO2 > 20% by increasing agitation speed. | |
| | aeration: 1 VVM | |
| | Feed profile: 3 g/l × h 0–24 hours. | |
| | 6 g/l × h 24–144 - | |
| | Inoculated with 50 ml 24 hour-old ASP03 shake flask culture. | |

During sterilisation the pH was increased to 10.5 for tank medium and/or feed medium (if supplied with hemoglobin). The hemoglobin was autoclaved at 121° C. for 40 min. at pH 10.5. Before fermentation, the pH was adjusted to 7,8.

The results appear from the table below.

| Fermentation no. | Conc of hemoglobin in | | Peroxidase yield after 144 hours (in %)* |
|---|---|---|---|
| | tank medium | feed medium | |
| 74 | 0 g/l | 0 g/l | 100 |
| 78 | 1 g/l | 0 g/l | 117 |
| 79 | 5 g/l | 5 g/l | 250 |
| 115 | 5 g/l (red blood cells) | 10 g/l | 300 |
| 26 | (hemin sterile filtr.) 50 mg/l | | 117 |

*The yield of peroxidase in medium without added hemoglobin is arbitrarily set at 100%

It appears from the table that the yield of peroxidase can be increased significantly by adding hemoglobin to the fermentation medium. It have not been possible to obtain the same degree of yield increase with hemin.

We claim:

1. A process for the extracellular production of a heterologous heme protein in a strain of Aspergillus sp., the process comprising:
   (a) transforming a suitable strain of an Aspergillus sp. with a recombinant DNA vector which comprises a DNA sequence encoding a heterologous heme protein, and a DNA sequence encoding a preregion permitting secretion of the expressed heme protein, and
   (b) culturing the transformed strain of Aspergillus sp. in a suitable culture medium under conditions conducive to the production of the heme protein.

2. A process according to claim 1, wherein the heme protein produced by the Aspergillus sp. in step (b) is subsequently recovered from the culture.

3. A process according to claim 1, wherein the Aspergillus sp. is *Aspergillus oryzae*.

4. A process according to claim 1, wherein the preregion is derived from a gene encoding an Aspergillus sp amylase.

5. A process according to claim 1, wherein the preregion is derived from the gene encoding *A. oryzae* TAKA amylase, *A. niger* neutral α-amylase, *A. niger* acid-stable α-amylase, *A. niger* glucoamylase, or the peroxidase produced by *Coprinus cinereus* or macrorhizus.

6. A process according to any of claims 1, wherein the heme protein is an oxidoreductase.

7. A process according to claim 6, wherein the oxidoreductase is a peroxidase or a haloperoxidase.

8. A process according to claim 7 wherein the DNA sequence encoding the peroxidase is derived from a Coprinus sp., in particular *Coprinus macrorhizus* or *cinereus*.

9. A process according to claim 1, wherein the culture medium comprises hemin or a heme-containing material.

10. A process according to claim 9, wherein said hemin is present in the medium at a concentration of between 1 and 1000 µg/ml.

11. A process according to claim 9, wherein said heme-containing material is selected from the group consisting of hemoglobin and red blood cells.

* * * * *

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 1307 base pairs
      (B) TYPE: nucleic acid
      (C) STRANDEDNESS: single
      (D) TOPOLOGY: linear (xi) SEQUENCE DESCRIPTION: SEQ ID NO:1:

```
TACTATGAAG CTCTCGCTTT TGTCCACCTT CGCTGCTGTC ATCATCGGTG CCCTCGCTCT      60

ACCCCAGGGT CCTGGAGGAG GCGGGTCAGT CACTTGCCCC GGTGGACAGT CCACTTCGAA     120
```

```
CAGCCAGTGC TGCGTCTGGT TCGACGTTCT AGACGATCTT CAGACCAACT TCTACCAAGG       180

GTCCAAGTGT GAGAGCCCTG TTCGCAAGAT TCTTAGAATT GTTTTCCATG ACGCGATCGG       240

ATTTTCGCCG GCGTTGACTG CTGCTGGTCA ATTCGGTGGT GGAGGAGCTG ATGGCTCCAT       300

CATTGCGCAT TCGAACATCG AATTGGCCTT CCCGGCTAAT GGCGGCCTCA CCGACACCGT       360

CGAAGCCCTC CGCGCGGTCG GTATCAACCA CGGTGTCTCT TTCGGCGATC TCATCCAATT       420

CGCCACTGCC GTCGGCATGT CCAACTGCCC TGGCTCTCCC CGACTTGAGT TCTTGACGGG       480

CAGGAGCAAC AGTTCCCAAC CCTCCCCTCC TTCGTTGATC CCCGGTCCCG GAAACACTGT       540

CACTGCTATC TTGGATCGTA TGGGCGATGC AGGCTTCAGC CCTGATGAAG TAGTTGACTT       600

GCTTGCTGCG CATAGTTTGG CTTCTCAGGA GGGTTTGAAC TCGGCCATCT TCAGGTCTCC       660

TTTGGACTCG ACCCCTCAAG TTTTCGATAC CCAGTTCTAC ATTGAGACCT TGCTCAAGGG       720

TACCACTCAG CCTGGCCCTT CTCTCGGCTT TGCAGAGGAG CTCTCCCCCT TCCCTGGCGA       780

ATTCCGCATG AGGTCCGATG CTCTCTTGGC TCGCGACTCC CGAACCGCCT GCCGATGGCA       840

ATCCATGACC AGCAGCAATG AAGTTATGGG CCAGCGATAC NNNNNNNNCA TGGCCAAGAT       900

GTCTGTTCTC GGCTTCGACA GGAACGCCCT CACCGATTGC TCTGACGTTA TTCCTTCTGC       960

TGTGTCCAAC AACGCTGCTC CTGTTATCCC TGGTGGCCTT ACTGTCGATG ATATCGAGGT      1020

TTCGTGCCCG AGCGAGCCTT TCCCTGAAAT TGCTACCGCC TCAGGCCCTC TCCCCTCCCT      1080

CGCTCCTGCT CCTTGATCTG GTGAAGATGG TACATCCTGC TCTCTCATCA TCCCTCTTAG      1140

CTATTTATCC AATCTATCTA CCTATCTATG CAGTTTCTGT TCTATCACCA CAGGAAGCAA      1200

GAAAGAAAAA CAACAATGCA ACGTGAGCAG AAATCAGCAA AAAAATAAAT CAGTATACTA      1260

CAGTAATGAG GCCAGTTTGC GTGGTGTCAG AAGTAAGTAC GACTCGG                   1307

(2) INFORMATION FOR SEQ ID NO:2:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO:2:

GCGCGAATTC GTNGGNATNA ACCACGG                                           27

(2) INFORMATION FOR SEQ ID NO:3:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO:3:

GCGGATCCGG NGGGCAGTTN GACAT                                             25

(2) INFORMATION FOR SEQ ID NO:4:

(i) SEQUENCE CHARACTERISTICS:
        (A) LENGTH: 28 base pairs
        (B) TYPE: nucleic acid
```

```
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO:4:

GCGAATTCAC NCCNCAGGTN TTCGACAC                                              28

(2) INFORMATION FOR SEQ ID NO:5:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO:5:

GCGGATCCGA ACTCNCCNGG GAANGG                                                26

(2) INFORMATION FOR SEQ ID NO:6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO:6:

GCGCGAATTC TGGCAGTCNA C                                                     21

(2) INFORMATION FOR SEQ ID NO:7:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO:7:

GCGCGAATTC TGGCAGAGNA TG                                                    22

(2) INFORMATION FOR SEQ ID NO:8:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO:8:

GGATCCGACA TCTTNGCCAT NGC                                                   23
```

(2) INFORMATION FOR SEQ ID NO:9:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO:9:

GTCTCGATGT AGAACTG    17